United States Patent
Wetegrove et al.

(10) Patent No.: US 6,750,328 B1
(45) Date of Patent: *Jun. 15, 2004

(54) ANTIBODIES FOR DETECTION OF WATER TREATMENT POLYMERS

(75) Inventors: Robert L. Wetegrove, Winfield, IL (US); James W. Stave, Elkton, MD (US); Robert J. Carlin, Newark, DE (US); Krishna Balakrishnan, Richmond, CA (US); Ming-Hsien Wu, Sherman Oaks, CA (US)

(73) Assignee: Strategic Diagnostics, Inc., Newark, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/506,793

(22) Filed: Jul. 25, 1995

Related U.S. Application Data

(63) Continuation-in-part of application No. 08/132,600, filed on Oct. 4, 1993, now Pat. No. 5,593,850, which is a continuation-in-part of application No. 07/786,154, filed on Oct. 31, 1991, now abandoned, and a continuation-in-part of application No. 07/752,746, filed on Aug. 30, 1991, now abandoned.

(51) Int. Cl.$^7$ .................. C07K 21/08; C07K 16/00; G01N 33/53; G01N 33/543
(52) U.S. Cl. .............. 530/388.9; 530/389.8; 435/7.1; 435/7.9; 435/7.92; 436/518; 436/536; 436/547; 436/548
(58) Field of Search ............ 435/7.1, 7.9, 7.92, 435/7.93, 7.94, 7.95; 436/518, 547, 548; 530/387.1, 388.1, 388.85, 389.1, 389.8

(56) References Cited

U.S. PATENT DOCUMENTS

| | | | |
|---|---|---|---|
| 4,752,443 A | | 6/1988 | Hoots et al. |
| 4,756,881 A | | 7/1988 | Hoots et al. |
| 5,593,850 A | * | 1/1997 | Wetegrove et al. ........ 435/7.92 |
| 6,146,903 A | * | 11/2000 | Weatherbury et al. ...... 436/548 |
| 6,420,530 B1 | * | 7/2002 | Weatherby et al. ...... 530/388.9 |

FOREIGN PATENT DOCUMENTS

| | | | |
|---|---|---|---|
| EP | 0559249 | * | 2/1992 |

* cited by examiner

*Primary Examiner*—Padmashri Ponnaluri
(74) *Attorney, Agent, or Firm*—Kilpatrick Stockton LLP

(57) ABSTRACT

The invention provides an antibody having an affinity to water treatment polymers. The antibodies of the invention are used in assays to determine the presence or concentration of a water treatment polymer in a fluid or aqueous system.

11 Claims, 15 Drawing Sheets

ANTIBODIES FOR DETECTION OF WATER TREATMENT POLYMERS

REFERNCE TO RELATED PATENT

The present application is a continuation-in-part of U.S. patent application Ser. No. 08/132,600 filed Oct. 4, 1993, now issued U.S. Pat. No. 5,593,850, the disclosure of which is incorporated herein by reference, which is a continuation-in-part of U.S. patent application Ser. No. 07/752,746, filed Aug. 30, 1991, now abandoned, and U.S. patent application Ser. No. 07/786,154, filed Oct. 31, 1991 now abandoned.

BACKGROUND OF THE INVENTION

1. Field of the Invention

The invention relates generally to antibody assays, and more particularly, to monoclonal antibodies and antibody assays for the detection of cationic, anionic and nonionic water treatment polymers.

2. Description of the Prior Art

As described in U.S. Pat. Nos. 4,756,881 and 4,752,443, water-soluble sulfonated copolymers of acrylic acid and acrylamide (hereinafter referred to as "sulfonated copolymers") are used in the treatment of industrial cooling water to prevent corrosion and mineral deposits (scale). Generally, the active sulfonated copolymers remove dissolved minerals from the cooling water by complexing with the mineral. Over time, the complexation sites of the sulfonated copolymer molecules become saturated and the copolymer molecules become inactive, unable to remove any additional minerals from the cooling water.

To prevent corrosion and scale damage to machinery, as the polymers are inactivated they must be removed and replaced by active sulfonated copolymer. Thus, active sulfonated copolymer must be continually fed into the cooling water to replace the inactive sulfonated copolymer. Maintaining the proper feed level for the active sulfonated copolymer is essential for optimum performance of the cooling water system. An improper feed rate can lead to serious problems. For example, insufficient active sulfonated copolymer can result in the water treatment being overwhelmed by dissolved minerals, thereby causing severe corrosion or scale deposit. On the other hand, maintaining too high a level of the active polymer is very expensive and is an inefficient method for treating industrial cooling water.

Although several methods are available for determining the total concentration of sulfonated copolymer in an industrial cooling water system, i.e., active plus inactive sulfonated copolymer, these techniques are unsatisfactory since they only determine the concentration of total sulfonated copolymer, and do not measure the concentration of the active sulfonated copolymer. Moreover, these methods suffer from lack of specificity or poor sensitivity. For example, the older methods for detecting sulfonated copolymers include colloid titration with PVSK, complexation with Hyamine 1622, or reaction of excess magnesium with chrome azurol S. The above tests detect any polyanionic material and have a detection threshold of about 50 ppm polymer. Presently, the total amount of active sulfonated polymer in an industrial cooling water system cannot be inexpensively and rapidly determined.

Cationic polymers are also useful in many areas of industrial water treatment. These areas include paper manufacture, effluent stream clarification, sludge dewatering, mineral process and many others. Excessive amounts of cationic polymers may cause problems in waters discharged to the environment. It is therefore desirable to know with specificity and precision the amount of residual cationic polymer in a sample. Many prior art methods of determining cationic polymer concentrations in waste water and other water treatment systems suffer from lack of specificity or poor sensitivity as with the sulfonated copolymers described above. Desirably, a method that would solve the problems of sensitivity and specificity described for all types of polymer would be available.

SUMMARY OF THE INVENTION

One aspect of the present invention is directed to a monoclonal antibody having an affinity to water treatment polymers. These polymers may be sulfonated copolymers of acrylamide and acrylic acid or any generally available water treatment polymer. The monoclonal antibodies of the present invention have an absolute specificity for the water treatment polymer and a lower limit of detection in the femtogram per ml range when used in some detection formats.

The monoclonal antibodies of the invention are produced by hybridoma cell lines. One preferred hybridoma cell line of the invention is hybridoma cell line 6E2-H1-G4. Another preferred hybridoma cell line of the invention is hybridoma cell line 6D12-H9-H3. Still other preferred cell lines include M11.2 and D8.2.

Another aspect of the invention is directed to a method of manufacturing a monoclonal or polyclonal antibody having an affinity to a water treatment polymer. The inventive method includes the steps of: a) immunizing a mammal with a substance that will elicit an antibody response to a water treatment polymer attached to a carrier protein; b) preparing a hybridoma cell producing the monoclonal antibody from cells removed from the immunized mammal; c) cloning the hybridoma cell to produce a hybridoma cell line; and d) extracting the monoclonal antibody from the hybridoma cell line. According to one preferred embodiment of the invention, the mammal is a mouse.

A further aspect of the invention is directed to a process for the determination of the presence or concentration of a water treatment polymer in a fluid. The inventive process includes the step of incubating a sample of the fluid containing the water treatment polymer with a monoclonal or polyclonal antibody having an affinity for the water treatment polymer.

DESCRIPTION OF THE PREFERRED EMBODIMENTS

Figure 1:
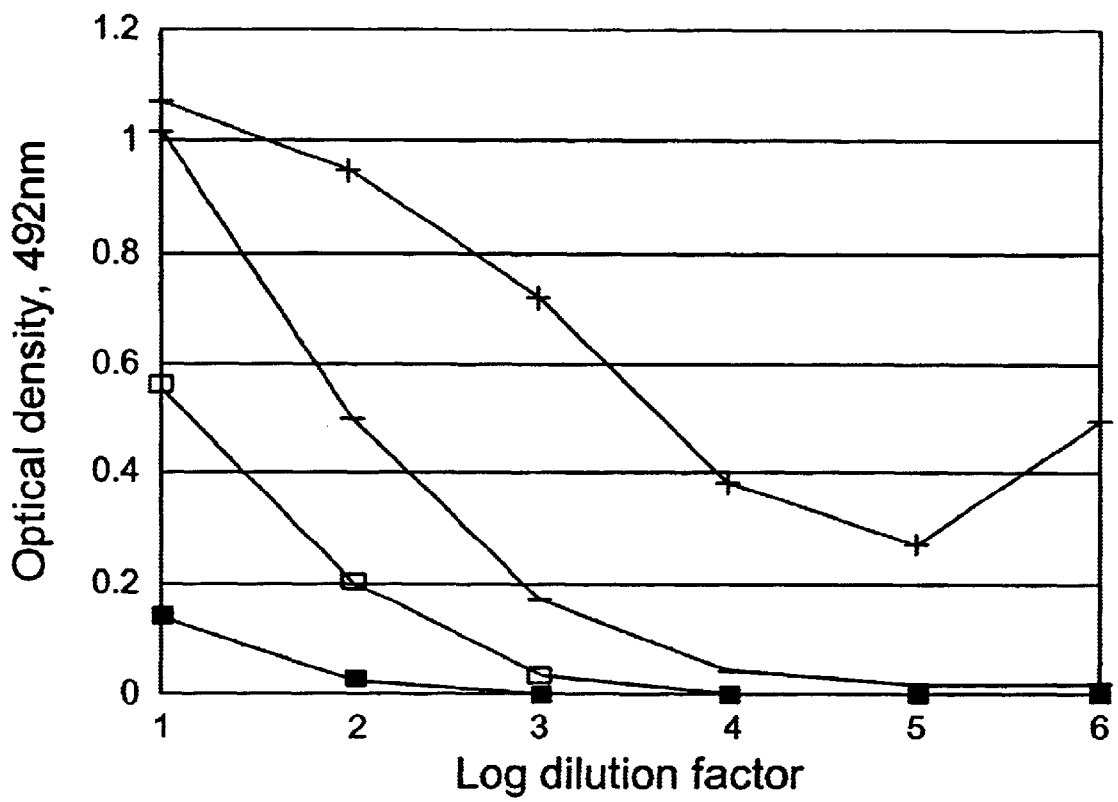
FIG. 1 is a graphic illustration of the binding profile of the monoclonal antibody from hybridoma cell line 6E2-H1-G4 to the sulfonated copolymer of acrylic acid and acrylamide conjugated to bovine serum albumin (BSA-SCP)—, the non-sulfonated copolymer of acrylic acid and acrylamide conjugated to bovine serum albumin (BSA-CP)—, the sulfonated copolymer of acrylic acid and acrylamide (SCP)—, and to a control bovine serum albumin (BSA)—.

Hybridoma cell lines producing antibodies having an affinity for water treatment polymer are herein described and claimed. The antibodies of the invention may be either monoclonal or polyclonal. Monoclonal antibodies are derived from a single cell, whereas polyclonal antibodies are derived from a number of cells. The antibodies of the invention bind to water treatment polymers with varying degrees of specificity.

By using two different assay formats, it has been conclusively proven that these antibodies can recognize SCP at concentrations ranging from zero to a few hundred parts per million. Examples described herein demonstrate the feasibility of using the monoclonal antibodies of the invention to determine the presence or concentration of SCP in fluids, such as water samples from industrial cooling water towers.

According to one embodiment of the invention, an antibody having an affinity to a water treatment polymer is used in an Immunosorbent Assay (ISA) for determining the concentration of water treatment polymer in a fluid sample. ISA formats using the antibodies of the invention are preferred for measuring the concentration of water treatment polymer in fluid samples. Three preferred immunoassay strategies are sandwich ISA, competition ISA and indirect ISA. Although several antibodies described herein are useful in assaying water treatment polymer in a fluid sample, the most preferred monoclonal antibodies are those produced by hybridoma cell lines 6E2-H1-G4, 6D12-H9-H3, M11.2 and D8.2 since these clones have shown the greatest anti polymer specificity in indirect ISAs for various target water treatment polymers.

According to one preferred embodiment of the invention a sandwich ISA is used for measuring the concentration of water treatment polymer. A sandwich ISA assay comprises binding an antibody for the water treatment polymer to a solid carrier. This is known as the capture antibody. The antibody is then adsorbed to wells of 96-well microtiter plates. Test samples containing water treatment polymer are then added and allowed to bind to the capture antibody. In the next step, labelled anti-water treatment polymer antibody is added and allowed to bind to the exposed antigenic sites on the water treatment polymer molecules captured by the coating antibody. The order of addition of the antibodies and the water treatment polymer is unimportant. They may be added simultaneously, sequentially or in any other manner that mixes the compounds. The amount of labelled antibody retained after washing would therefore correlate directly with the amount of water treatment polymer in the sample. Higher sensitivity is normally associated with sandwich ISAs as opposed to other types of assays.

In a preferred embodiment of the invention, excess labelled antibody is washed free of the bound antibody-polymer-antibody complex. Preferably, the step of washing is carried out by any of a number of procedures. These procedures include filtration, magnetic separation, decanting, centrifugation or chromatography. The labelled antibody may be selected from any of a number of compounds including enzymes, colored particles, fluorescent molecules, luminescent molecules, metals and radioisotopes. Where enzymes are used, the level of enzyme label bound in each well will be quantitated by incubation with a chromogenic enzyme substrate and the resulting color change is measured. A standard curve is then generated using known concentrations of waste water treatment polymer.

In another preferred embodiment, a competition ISA is used to measure the concentration of water treatment polymer for a fluid sample. According to this embodiment, purified anti-water treatment polymer antibody is adsorbed onto wells of 96-well microtiter plates. Test samples containing water treatment polymer are added to the plates with known quantities of labelled water treatment polymer. The amount of labelled water treatment polymer retained after washing will be inversely proportional to the amount of water treatment polymer originally present in the test samples. This particular format has the advantage of being essentially a one-step assay with only one incubation period.

According to a still further embodiment of the invention, indirect ISA assay is utilized to measure the concentration of water treatment polymer in a fluid. According to the embodiment, known quantities of Bovine Serum Albumin (BSA) conjugate are adsorbed to replicate wells of 96 well microtiter plates. Next, various dilutions of the anti-water treatment polymer monoclonal antibody are allowed to bind to the immobilized water treatment polymer. Labelled antibody is added next and allowed to bind to the primary antibody.

In an enzyme-labelled immunoassay, a chromogenic substrate is then added which will be converted to a colored product by the bound enzyme. The resultant color change will be quantified by measuring the absorbance (optical density) at the appropriate wavelength. The amount of color change will be proportional to the amount of enzyme-labelled antibody retained and thus will correlate directly with the amount of anti-water treatment polymer antibody which was able to initially bind to the immobilized water treatment polymer. The results will yield the optimal concentration of anti-water treatment polymer antibody to use in the assay.

Having defined the appropriate concentration of antibody for an indirect ISA, inhibition of binding between the antibody and the water treatment polymer-coated microtiter plates by water treatment polymer present in solution is determined. The anti-water treatment polymer primary antibody will be incubated with various concentrations of water treatment polymer before being added to the water treatment polymer-coated microtiter plates. A standard curve is then prepared by plotting the percentage inhibition as a function of free water treatment polymer concentration. This method is carried out for each fixed quantity of immobilized water treatment polymer and the primary antibody. This assay format will be suitable if the standard curve shows a steep dose-response at the concentrations that are relevant to those which occur in water samples. It has the advantage of not requiring any additional purification or modification of the anti-water treatment polymer monoclonal antibody.

Any of the assays discussed above could be further developed and refined using other solid support systems such as coated tubes and polymer membranes. However, the sandwich ISA or the competition ISA formats are preferred since they could be designed as a "dipstick" assay. Nevertheless, any of the above assay formats are intended to be used with the monoclonal antibodies of the present invention to measure the concentration of water treatment polymer in a fluid sample.

In the preferred embodiment of the invention, polymers used in the treatment of water, may include acrylic acid/acrylamide co-polymers, sodium acrylate polymers, ammonium acrylate polymers, acrylamide homopolymers, acrylamide/dimethylaminoethylacrylate methylchloride quat co-polymers, acrylamide/dimethylaminoethylacrylate methylsulfate quat co-polymers, acrylamide/dimethylaminoethylmethacrylate methylchloride quat co-polymers, acrylamide/dimethylaminoethylmethacrylate methylsulfate quat co-polymers and sulfonated copolymers of acrylamide and acrylic acid.

In another embodiment of the invention coagulants used in the treatment of water systems may include epichlorohydrin/dimethylamine polymers, poly(diallyldimethylammonium chloride) polymers, ethylenedichloride/ammonium polymers, diallyldimethylammonium chloride/acrylic acid co-polymers, melamine formaldehyde co-polymers, and combinations of these polymers.

Finally, the use of the method of the invention in conjunction with commonly used chemically modified polymers with functionalities for metal ion complexation in the treatment of water systems is contemplated under the invention. Two examples of these polymers include dithiocarbamate and polymeric dithiocarbamate The following examples are presented to describe preferred embodiments and utilities of the invention and are not meant to limit the invention unless otherwise stated in the claims appended hereto.

EXAMPLE 1

The antigens were prepared as follows:

Twenty mg of the polymer was first derivatized with the coupling agent, 1-ethyl 3(3'-dimethylamino-propyl) carbodiimide (EDC) at a pH of 5.0. After a 15 minute incubation at room temperature, 15 mg of Keyhole Limpet Hemocyanin (KLH) or 10 mg of Bovine Serum Albumin (BSA) was added and allowed to react at pH 7.0 for 4 hours, also at room temperature. Small molecular weight side products were removed by overnight dialysis at 4° C.

Both sulfonated (SCP) and non-sulfonated (CP) forms of acrylate-acrylamide copolymers were tested. The sulfonated copolymer was obtained from Nalco Chemical Company under the tradename designation PRISM®. The non-sulfonated copolymer was also obtained from Nalco Chemical Company. High and low molecular weight fragments were tested for both forms. Exact molecular weights of the copolymers were 6.6 kD and 23 kD for the non-sulfonated forms and 7.4 kD and 26 kD for the sulfonated forms. The smaller molecular weight copolymers, both sulfonated and non-sulfonated, were conjugated through carboxylic acid residues on the copolymers to amino groups on the carrier proteins KLH and BSA using the coupling agent EDC as described above. Gel electrophoresis of the BSA conjugate indicated successful conjugation with approximately one to four copolymer molecules conjugated per molecule of BSA. The KLH conjugates were too heterogeneous and less well defined to be meaningfully analyzed by electrophoresis.

Preferably, the immunogen of the invention is coupled to a protein. The use of an immunogenic protein increases antibody response from the immunized animal, resulting in a greater number of antibodies being produced. Preferably, the immunogen has a molecular weight of from about 50 to about 100,000 daltons. The protein would preferably be KLH or BSA.

EXAMPLE 2

The BSA conjugates of the lower molecular weight copolymers were tested for adsorption onto microtiter plates by performing an indirect ELISA using rabbit anti-BSA antiserum. Plates were coated with the conjugates at a concentration of 0.01 mg/ml (0.5 ug/well) in phosphate-buffered saline, pH 7.2 (PBS). Unoccupied sites on the plates were blocked with a 5% solution of non-fat milk in PBS. Dilutions of rabbit anti-BSA antiserum were incubated with the plate. Horseradish peroxidase (HRP) labelled goat anti-rabbit antibody was then allowed to bind to the primary anti-BSA antibody. The bound enzyme (HRP) was then quantitated with a chromogenic substrate. These assays were performed in duplicate, the results are tabulated in Table 1. These results clearly indicate that the BSA conjugates bound strongly to the ELISA plates, thus confirming the utility of these conjugates for the screening of anti-SCP antibodies in an indirect ELISA format.

TABLE 1

| Indirect ELISA with Rb anti-BSA sera | | | |
| --- | --- | --- | --- |
| Set | Antigen | $OD_{1/2max}$ | Titer value |
| #1 | SCP-BSA | 0.96 | 1:9000 |
|  | CP-BSA | 0.94 | 1:7100 |
|  | BSA | 0.87 | 1:14,000 |
|  | No Ag | 0.31 | 1:50 |
| #2 | SCP-BSA | 0.94 | 1:9000 |
|  | CP-BSA | 0.92 | 1:7700 |
|  | BSA | 0.86 | 1:13,000 |
|  | No Ag | 0.36 | <1:50 |

EXAMPLE 3

Immunization of four groups (A–D) of female Balb/c mice, five mice per group, approximately 9–12 weeks of age, was performed. Groups A and B were boosted weekly with 100 ug of SCP-KLH immunogen per mouse administered via intraperitoneal injection. Group A received immunogen emulsified in Freund's adjuvant, Group B received immunogen emulsified in Ribi's adjuvant. Groups C and D received weekly immunizations of 100 ug of unconjugated SCP immunogen per mouse emulsified in Freund's adjuvant or Ribi's adjuvant respectively. Mice were bled periodically and each serum sample was evaluated by indirect ELISA against SCP-BSA and CP-BSA. Antibody titer values were determined from the ELISA results; antibody titer being defined as the dilution of the sample sera which yields an optical density that is one-half of the maximum signal obtained ($OD_{1/2max}$) in an indirect ELISA. Table 1 presents the titer results obtained for all four groups of animals.

EXAMPLE 4

Mice with elevated antibody titer against SCP-BSA were sacrificed and the splenocytes were isolated and fused with Hypoxanthine Guanidine Phosphoribosyl Transferase (HGPRT) deficient SP 2/0 plasmacytoma cells utilizing polyethylene glycol (PEG) as the fusing agent. Fusion #1 was performed with the two mice from Group B which had titers of 1:11,000 and 1:14,000, respectively, against SCP-BSA. Their corresponding titer values against CP-BSA were 1:4700 and 1:6700. Fusion #2 was performed using two mice from Group E (an additional group of mice which was subsequently started) with anti-SCP-BSA titer values of 1:2600 and 1:2900 respectively. Their corresponding titer values against CP-BSA were 1:1000 and 1:920. The fused cells were plated into 96-well tissue culture plates and the resultant hybridomas were identified by selection in Hypoxanthine Aminopterin Thymidine (HAT) medium. The hybridoma cell lines developed which produced anti-SCP monoclonal antibodies were 6E2-H1-G4, 6D12-H9-H3, 6C8-F1-F9, 4D4-C9-F6, 4B1-H6-E10 and 4F12-C12.

EXAMPLE 5

Hybridoma cell lines 6E2-H1-G4 and 6D12-H9-H3 were scaled up by growing them in vitro for several passages and injecting them into a group of pristane-primed Balb/c mice. The cells grew as ascites tumors in these mice and the resultant fluid accumulated in their peritoneal cavities was harvested. The ascites fluid was enriched in the desired anti-SCP antibody which was purified and used in the assays described below.

EXAMPLE 6

Depending on the assay format being pursued, antibodies will be required either as unpurified ascites or as a highly purified immunoglobulin preparation. Antibodies were purified from ascites fluid by a variety of methods, depending on the antibody isotype and the sensitivity of the antibody to various buffers. The clones 6E2-H1-G4 and 6D12-H9-H3 identified in Example 5 are of the IgG isotype, and accordingly, they were purified by using the pseudo-affinity matrix Protein A.

EXAMPLE 7

Table 2 summarizes the binding data for the different hybridoma cell lines that were developed. All the cell lines were subcloned by limiting dilution in the presence of appropriate growth factors. When clonel populations of cells were identified, the supernatants were assayed again for SCP binding and single colonies that exhibited the required binding specificity were expanded and frozen down.

TABLE 2

ANTI-SCP HYBRIDOMAS. BINDING DATA

| No. | Cell line | ELISA Signal of parent | | ELISA Signal of clone | |
| --- | --- | --- | --- | --- | --- |
| | | SCP | CP | SCP | CP |
| 1 | 6D12 H9-H3 | 1.70 | 0.11 | 1.48 | 0.02 |
| 2 | 6C8-F1-F9 | 0.92 | 0.02 | 0.77 | 0.00 |
| 3 | 4D4-C9-F6 | 0.77 | 0.18 | 0.61 | 0.12 |
| 4 | 6E2-H1-G4 | 2.00 | 0.11 | 1.81 | 0.45 |
| 5 | 4B1-H6-E10 | 1.39 | 0.50 | 1.74 | 0.55 |
| 6 | 4F12-C12 | 1.46 | 0.16 | 1.48 | 1.38 |

EXAMPLE 8

The binding specificity of the different anti-SCP monoclonal antibodies was tested by an indirect ELISA. Replicate wells were coated with 500 ng per well of the following panel of antigens: BSA-SCP, BSA-CP, SCP or BSA. Serial dilutions of the ascites fluid ranging from 1:10 to $1:10^6$ in steps of 10 were incubated with the various antigen coated plates. After an incubation with the ascites fluid samples, the plates were washed and incubated with HRP-labelled goat anti-mouse Ig. Finally, the quantity of enzyme (HRP) retained in each well was quantified using $H_2O_2$ and a chromogenic substrate. The optical density readout at 492 nm was recorded using an automated ELISA reader and the results are summarized in FIGS. 1, 2, and 3.

Figure 2:
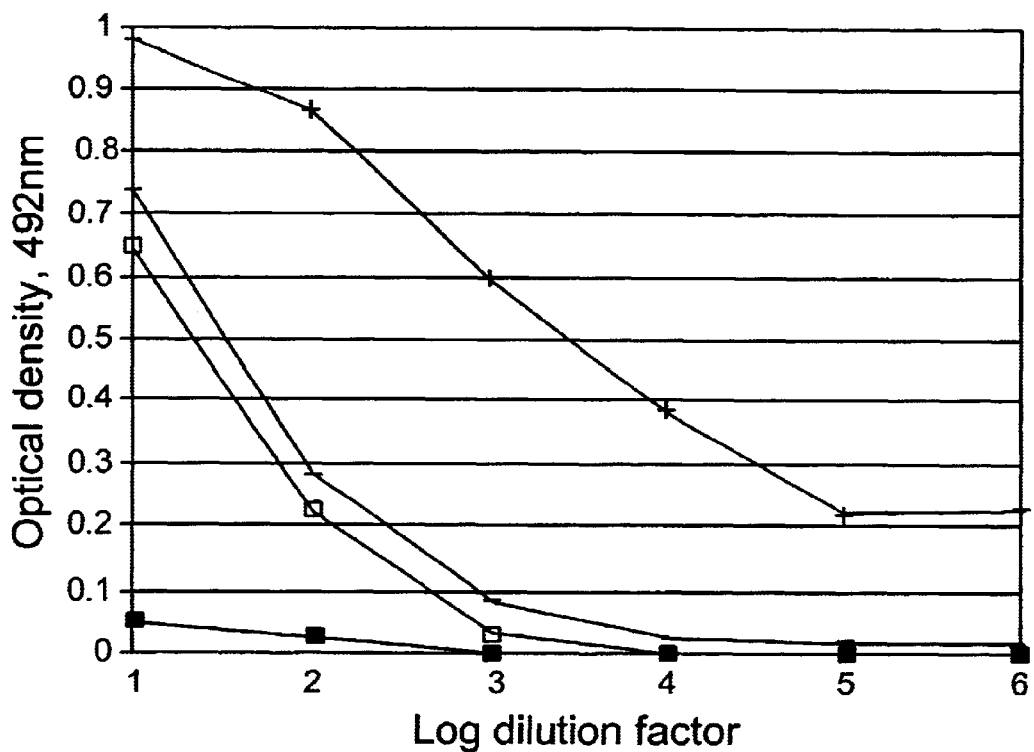
FIG. 2 graphically illustrates the binding profile of the monoclonal antibody from the hybridoma cell line 6D12-H9-H3 to BSA-SCP—, BSA-CP—, SCP—, and BSA—.
Figure 3:
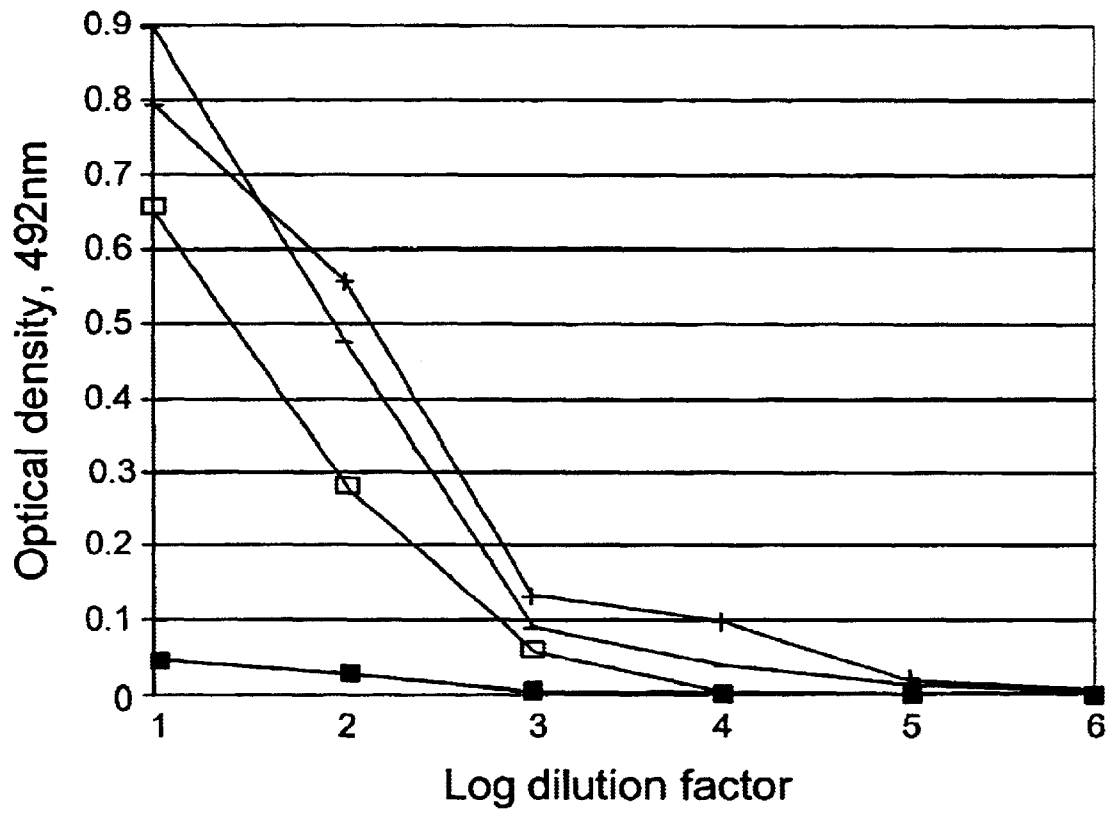
FIG. 3 is a graphic illustration of the binding profile of the monoclonal antibody from hybridoma cell line 4D4-C9-F6 to BSA-SCP—, BSA-CP—, SCP—, and BSA—.

Of the three different monoclonal antibodies whose results are shown in FIGS. 1, 2, and 3, cell lines 6E2-H1-G4 and 6D12-H9-H3 show a dramatically higher binding specificity for BSA-SCP as compared to BSA-CP whereas cell line 4D4-C9-F6 is almost equally reactive to BSA-SCP and BSA-SP. These results confirm the earlier findings shown in Table 1, where these studies were carried out with spent tissue culture supernatants from these cell lines.

EXAMPLE 9

Based on the information obtained from the indirect ELISA results, summarized in FIGS. 1, 2, and 3, two of the cell lines 6E2-H1-G4 and 6D12-H9-H3 which produced monoclonal antibody that showed specificity to BSA-SCP are the preferred cell lines of the invention. The results for the indirect ELISA were used to calculate the optimal concentrations of the two different monoclonal antibodies which would produce the most sensitive results in an inhibition ELISA. The inhibition ELISA carried out in this set of experiments is briefly described below.

Figure 4:
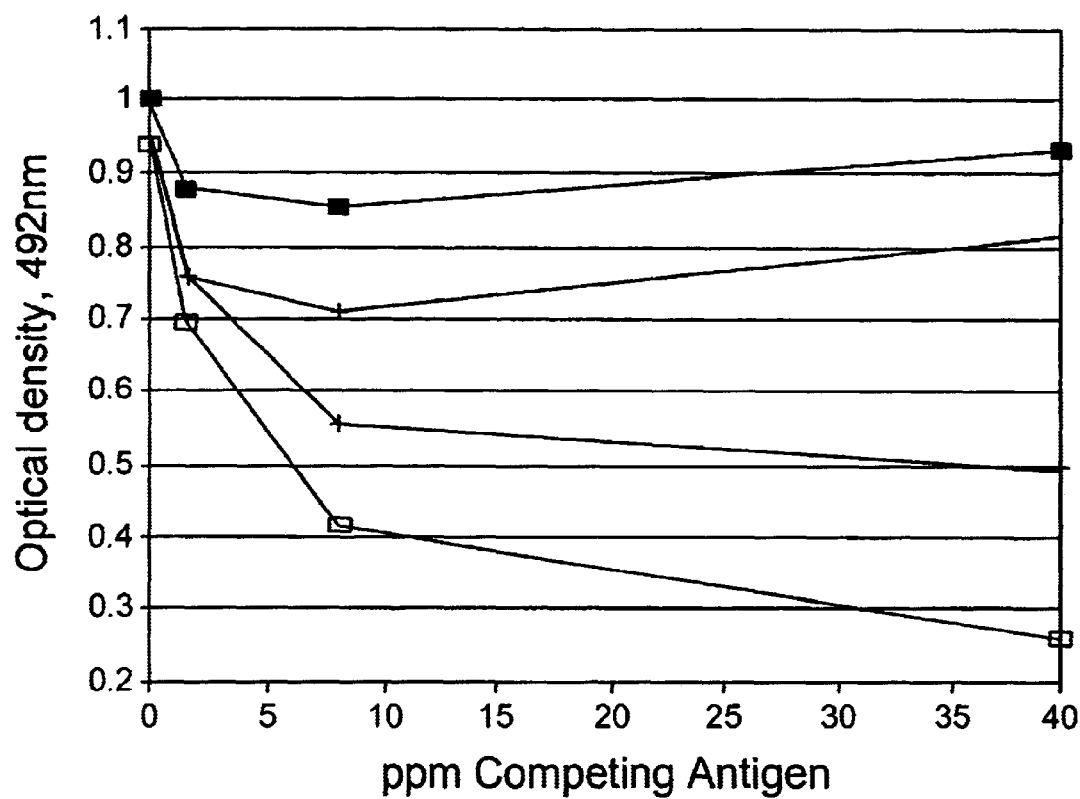
FIG. 4 is a graphic illustration of an inhibition Enzyme Linked Immunosorbent Assay (ELISA) assay using the monoclonal antibody from the hybridoma cell line 6D12-H9-H3, wherein — is BSA, — is CP, — is SCP, and — is BSA-SCP.
Figure 5:
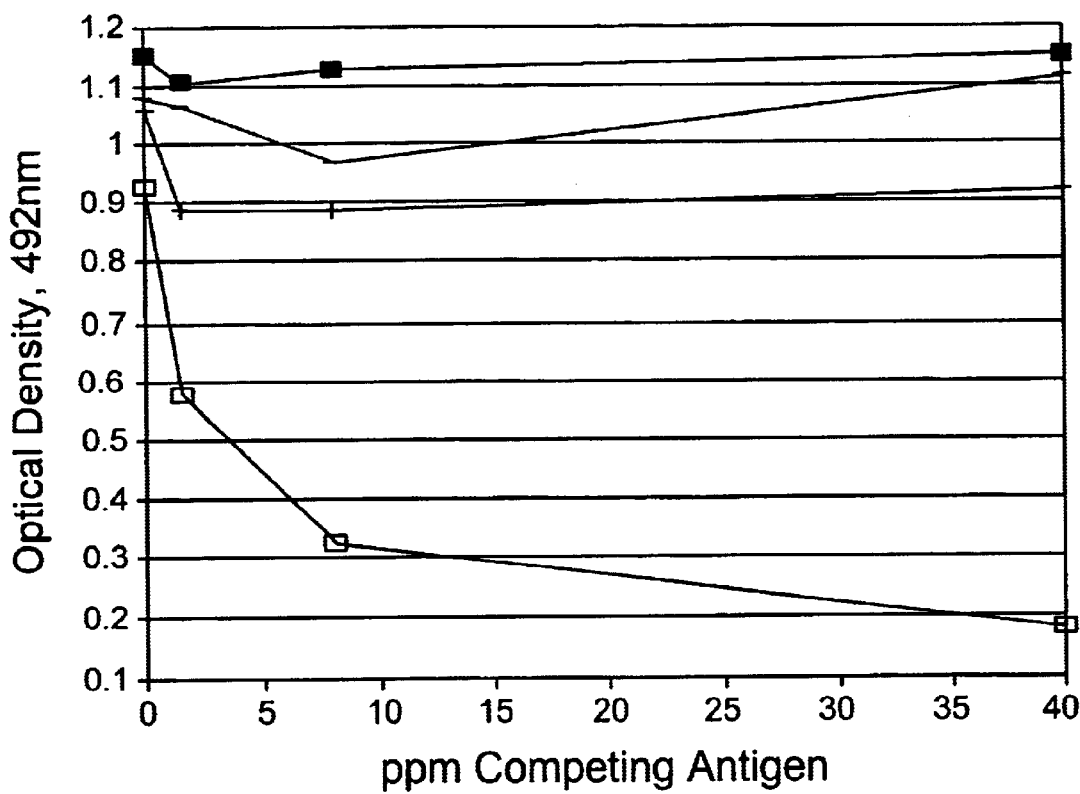
FIG. 5 is a graphic illustration of an inhibition ELISA assay using the monoclonal antibody from the hybridoma cell line 6E2-H1-G4, wherein — is BSA, — is CP, — is SCP, and — is BSA-SCP.

Microtiter plates were coated with 500 ng per well of BSA-SCP and non-specific sites on the plate were blocked. Replicate samples of the test ascites fluid at a fixed concentration were preincubated with increasing concentrations of a panel of competing antigens for 2 hrs at room temperature. After this preincubation, the antibodies were allowed to bind to the BSA-SCP coated plates. The panel of antigens used in the competition ELISA included BSA-SCP, SCP, CP or BSA. The object of the assay was to demonstrate the antibody specificity in a solution phase assay. A highly specific antibody would bind tightly with the cognate antigen in solution and not the others. This would result in an inhibition of the antibody from binding to the BSA-SCP coated plate only in the presence of the appropriate antigen and not the others. The quantity of anti-SCP monoclonal antibody bound to the BSA-SCP coated plate was determined as before with the use of an HRP-labelled goat anti-mouse Ig and a chromogenic substrate for HRP. Results of such assays are shown in FIGS. 4 and 5. As seen from these figures, the two cell lines 6E2-H9-G4 and 6D12-H9-H3 do show considerable differences in the inhibition ELISA. Cell line 6D12-H9-H3 (shown in FIG. 4) detects approximately 5 to 40 ppm of SCP and distinguish it from SP. Cell line 6E2-H1-G4, as shown in FIG. 5, was not as sensitive, but could still be useful in an assay. All of the above assays were performed in phosphate buffered saline, pH 7.2.

EXAMPLE 10

Various aqueous samples containing SCP, acquired from Nalco Chemical Company, Naperville, Ill., under the trademark designation PRISM® polymer, were prepared. Some of the samples mimicked "field" conditions in that they contained fairly high concentration of $Fe^{+3}$ and $Ca^{+2}$ ions such that the SCP was substantially inactive. Also tested were samples which contained quantities of uncomplexed active SCP sufficient enough to prevent scaling.

Figure 6:
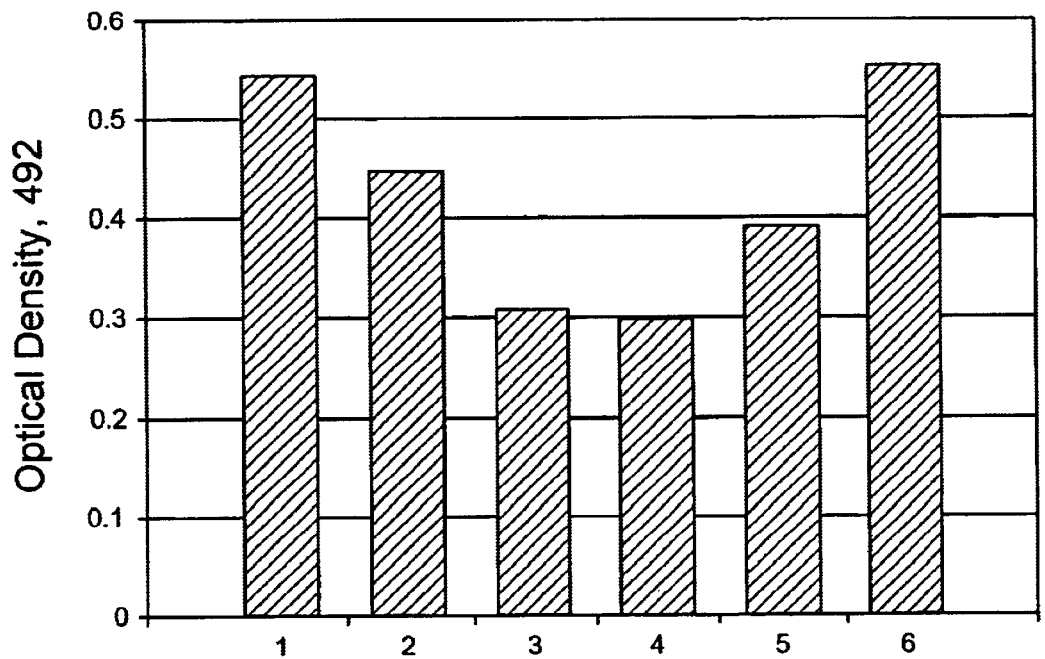
FIG. 6 is a graphic illustration of an inhibition ELISA assay using the monoclonal antibody from the hybridoma cell line 6D12-H9-H3 to detect active and inactive SCP in Phosphate Buffered Saline in (PBS) buffer, wherein group 1 includes only PBS, group 2 includes 10 ppm CP, group 3 includes 10 ppm SCP, group 4 includes 20 ppm SCP, group 5 includes 10 ppm SCP, and group 6 includes 10 ppm inactive SCP and 4 mMFe.
Figure 7:
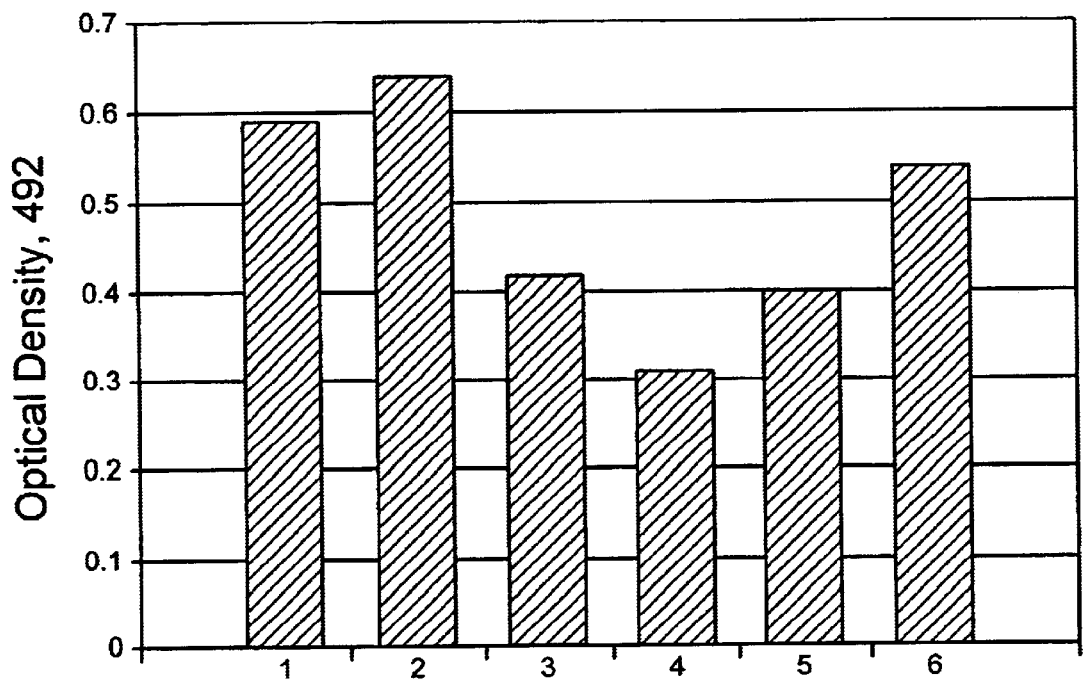
FIG. 7 is a graphic illustration of an inhibition ELISA assay using the monoclonal antibody from the hybridoma cell line 6D12-H9-H3 to detect active and inactive SCP in Tris Buffered Saline (TBS) buffer, wherein group 1 includes only TBS, group 2 includes 10 ppm CP, group 3 includes 10 ppm SCP, group 4 includes 20 ppm SCP, group 5 includes 10 ppm SCP, and group 6 includes 10 ppm inactive SCP and 4 mMFe.

A series of experiments were carried out to determine if the monoclonal antibodies of the invention could distinguish between an "active" and an "inactive" solution of SCP. Results of these experiments are shown in FIGS. 6 and 7. Parallel experiments were also carried out using phosphate buffered saline (PBS) and Tris buffered saline (TBS). As seen from FIGS. 6 and 7, the assay effectively distinguished between an "active" sample (sample 4) and an "inactive" sample (sample 6). In experiments shown in FIG. 6, the assays were carried out in PBS, whereas those shown in FIG. 7 utilized TBS. Samples 3 and 2, the positive and negative controls, contained 10 ppm of the SCP polymer and CP polymer respectively, and were made up in the respective buffers PBS and TBS. The samples were all diluted 1:2 with the appropriate buffer in the assay, either PBS or TBS and were composed of the following: Sample 1 included only PBS. Sample 4 contained 20 ppm of SCP and hence should be an "active" sample, in as much as it contained quantities of SCP sufficient enough to prevent scaling. Sample 5 contained 10 ppm of SCP and could also be considered "active" although with a lower polymer concentration. Sample 6 was prepared with 10 ppm SCP and 4 mM $Fe^{+3}$ in such a way to simulate an "inactive" sample. Sample 6 presumably will not prevent scaling and clearly could be identified as not containing any detectable quantity of free, active SCP.

The following examples show the use of the claimed invention in conjunction with various non-sulfonated water treatment polymers. The following names have been assigned to respective compositions. Polymer A is EDC—NH3, which is an ethylene dichloride ammonia condensation polymer. Polymer D is DMA-epi, which is a dimethylamine epichlorohydrin condensation polymer (not-crosslinked). Finally, Polymer E is a DMA-epi coagluant polymer blended with aqueous aluminum salts.

EXAMPLE 11

Work was done on the validation and development of immunoassays for detection of trace levels of water treatment polymer. Experiments with polymer analysis in waste and raw water samples were started using mixed liquor spiked with trace polymer A at different concentrations from approximately 10 to 1000 ppb; the responses from these spiked samples were compared with standards prepared in water. At detectable levels of polymer, mixed liquor suppressed the response. River water was analyzed and used in a standard addition study vs. distilled water. The river water had the following characteristics.

| | |
|---|---|
| Turbidity | 0.7 NTU |
| Apparent Color | 2 Co-Pt units |
| Apparent Color (filtered) | 1 Co-Pt units |
| DOC | 20.6 ppm |
| Alkalinity | 75 ppm |
| Conductivity | 0.217 mS/cm |

Figure 8:
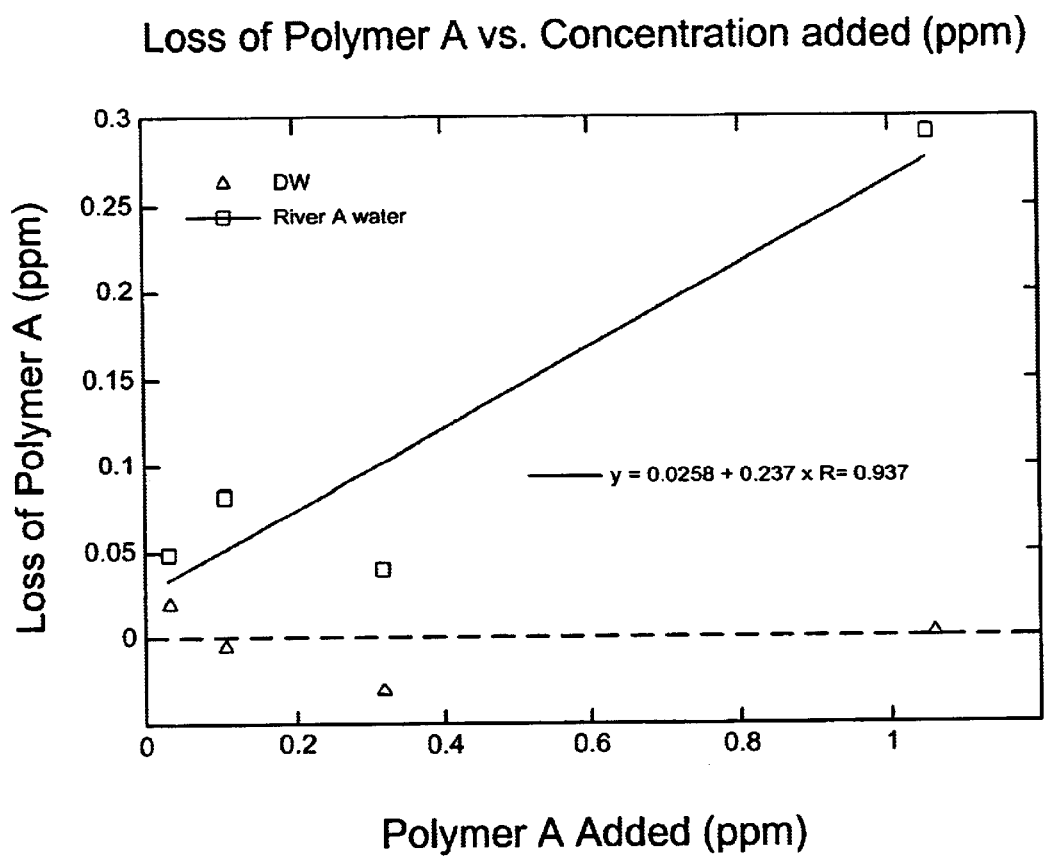
FIG. 8 is a graph showing a loss of Polymer A actives added to River A water across a range of concentrations.

The river water was spiked with trace polymer A over the concentration range of approximately 30 to 1000 ppb. Standard curves in distilled water were analyzed and used as a basis for calculating % recovery of polymer in the spiked river water samples. The % recovery observed is dependent upon the concentration of polymer added (See FIG. 8). Reproducible recovery of polymer was not observed until approximately 300 ppb of polymer had been added. The preliminary results suggest that this technique for free polymer analysis could be used to directly demonstrate the ability of a given raw water supply to bind polymer residual in a water treatment effluent stream. Free polymer recovery in raw water could be correlated with aquatic toxicity, to predict the critical limit for polymer concentration in effluent to meet regulatory guidelines.

EXAMPLE 12

Four more river water samples from Michigan were obtained for standard addition studies. The following measurements characterized the water samples:

| | River | | | |
|---|---|---|---|---|
| Measurement | A | B | C | D |
| DOC (ppm) | 9 | 13 | 6 | 10 |
| Apparent Color (PtCo units) | 64 | 39 | 66 | 60 |
| Filtered color (PtCo units) | 15 | 20 | 24 | 20 |
| Turbidity (FTU) | 9 | 7 | 12 | 11 |
| Conductivity (mS/cm) | 0.322 | 0.465 | 0.526 | 0.369 |
| pH | 8.3 | 8.2 | 8.1 | 8.2 |

Figure 9:
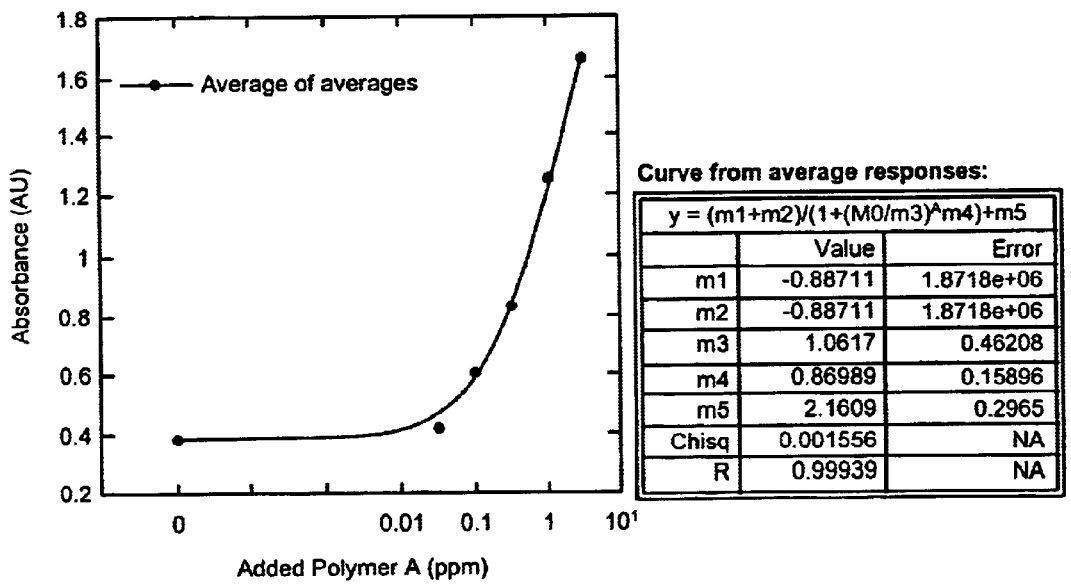
FIG. 9 is an average Polymer A standard curve in distilled water.
Figure 10:
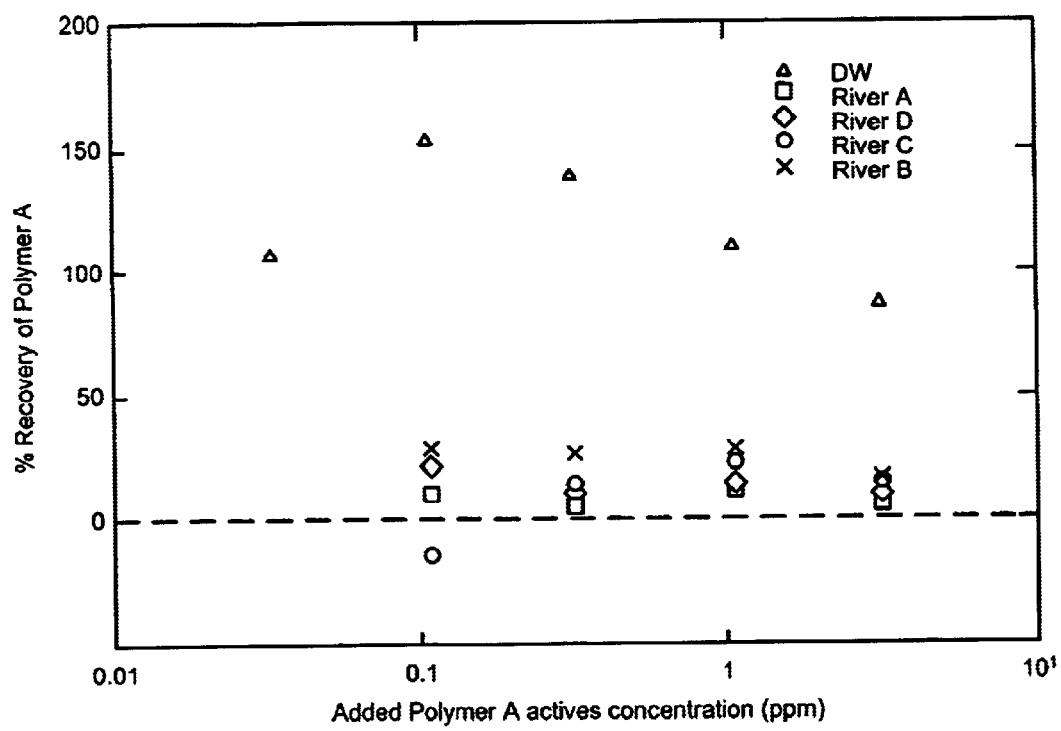
FIG. 10 is a graph showing the percent of Polymer A actives added to various river waters.
Figure 11:
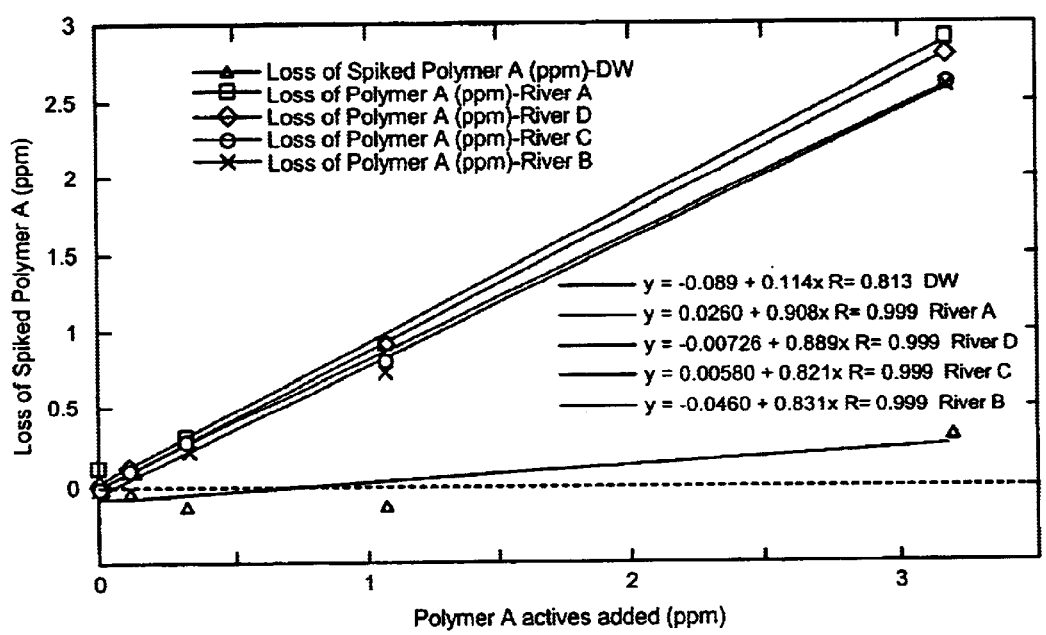
FIG. 11 is a graph showing the loss of Polymer A actives added to various river waters.

Each river sample was spiked with trace polymer A so that the final concentrations of actives added were: 106, 318, 1060, and 3180 ppb. These spiked samples, along with a blank sample of each water, were analyzed along with polymer A standards prepared in distilled water to concentrations of 32, 106, 318, 1060, and 3180 ppb of active polymer. FIG. 9 shows the resulting average calibration curve. Materials present in the water adsorb a significant amount of cationic polymer. The adsorbed amount equals the polymer capacity of the water. Low recoveries of trace polymer A spiked into these waters indicate such adsorption. The percent recovery of polymer A actives and the loss of polymer A actives in these river waters are shown in FIGS. 10 and 11. The linear (slope ≈0.9, r2≈0.999) relationship between polymer loss and concentration added is apparent and indicates that nearly complete consumption of polymer is occurring in the four river samples across the standard range tested. The magnitude of the slope represents the polymer capacity. A comparison of the slopes from these four rivers to the slope from the FIG. 8 sample shows that the "cleaner" river from FIG. 8 has a significantly lower slope.

EXAMPLE 13

Figure 12:
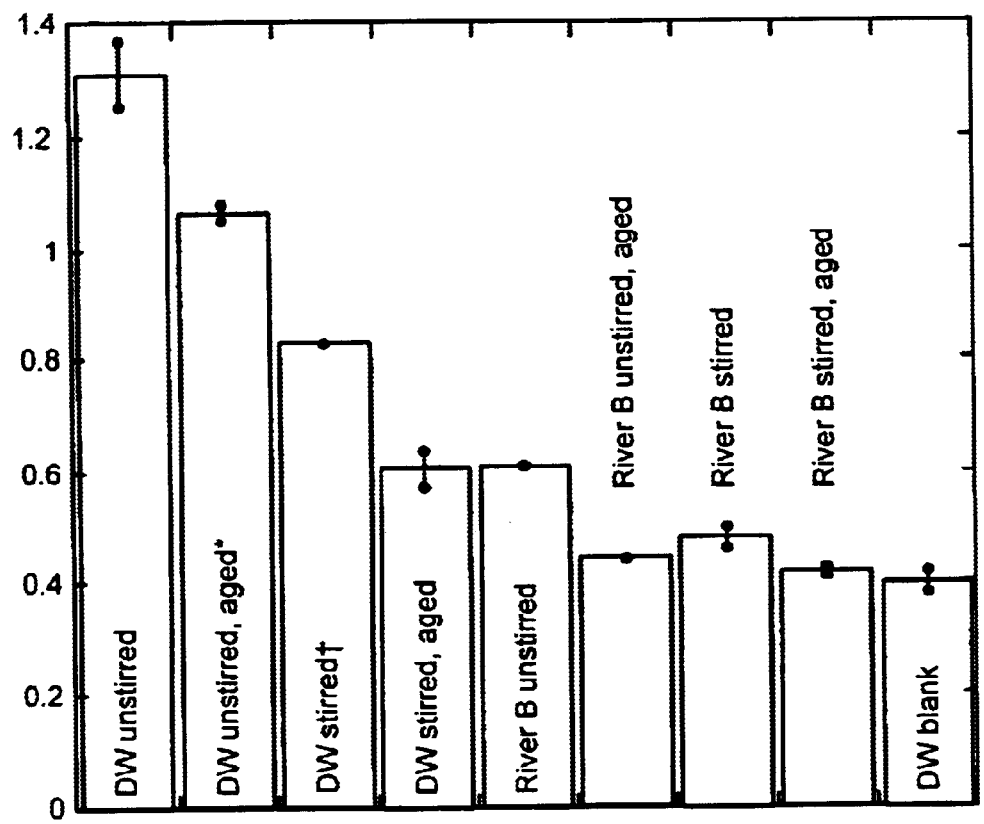
FIG. 12 is a graph showing the response by immunoassay for free polymer A for distilled water and River B water spiked with Polymer A actives.
Figure 13:
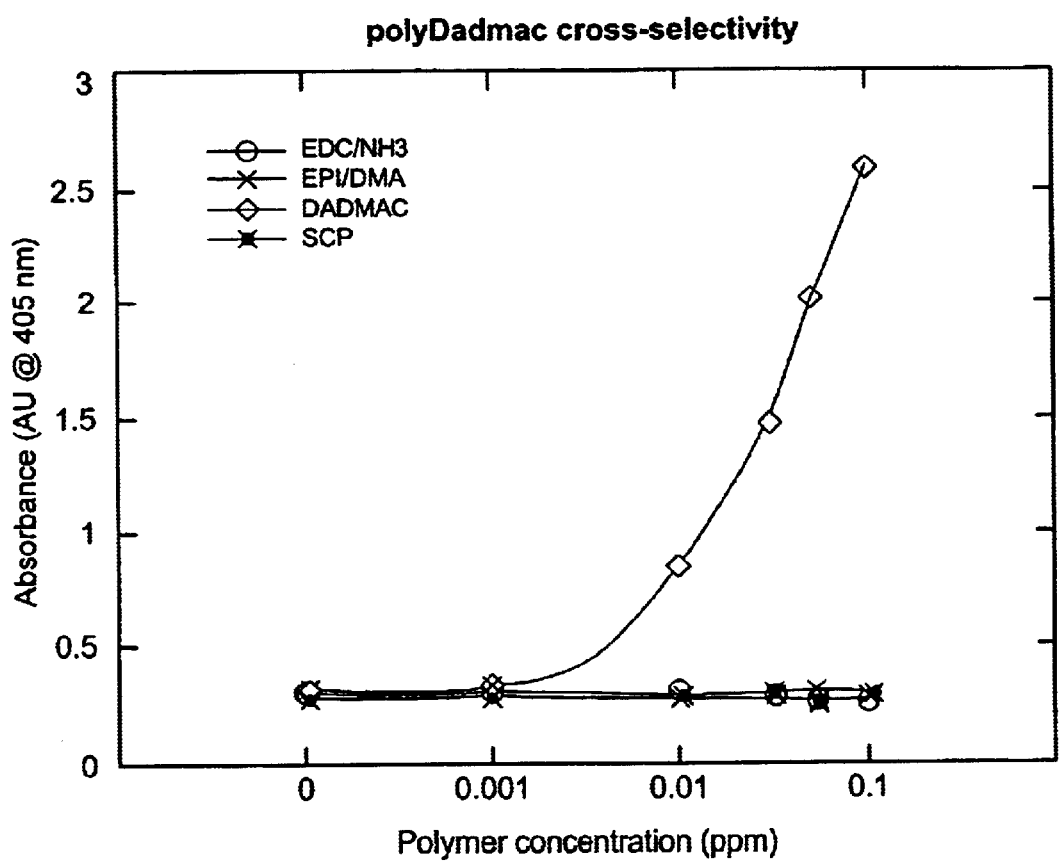
FIG. 13 graphically illustrates the binding profile of the monoclonal antibody from the hybridoma cell line M11.2.
Figure 14:
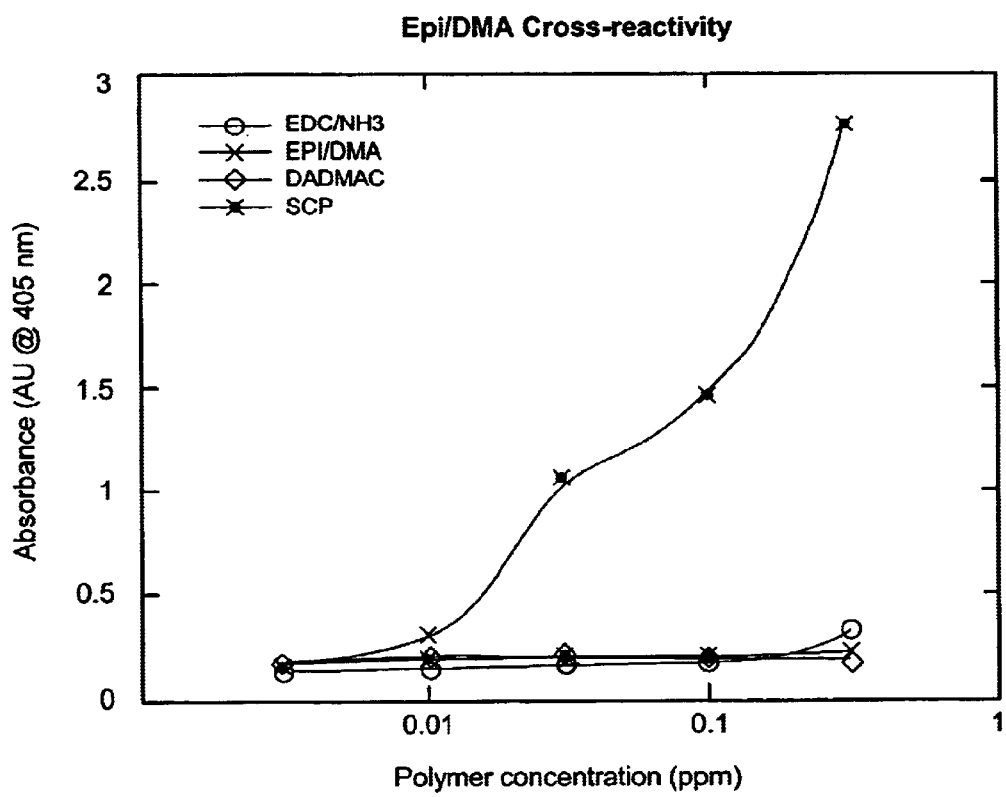
FIG. 14 graphically illustrates the binding profile of the monoclonal antibody from the hybridoma cell line D8.2.
Figure 15:
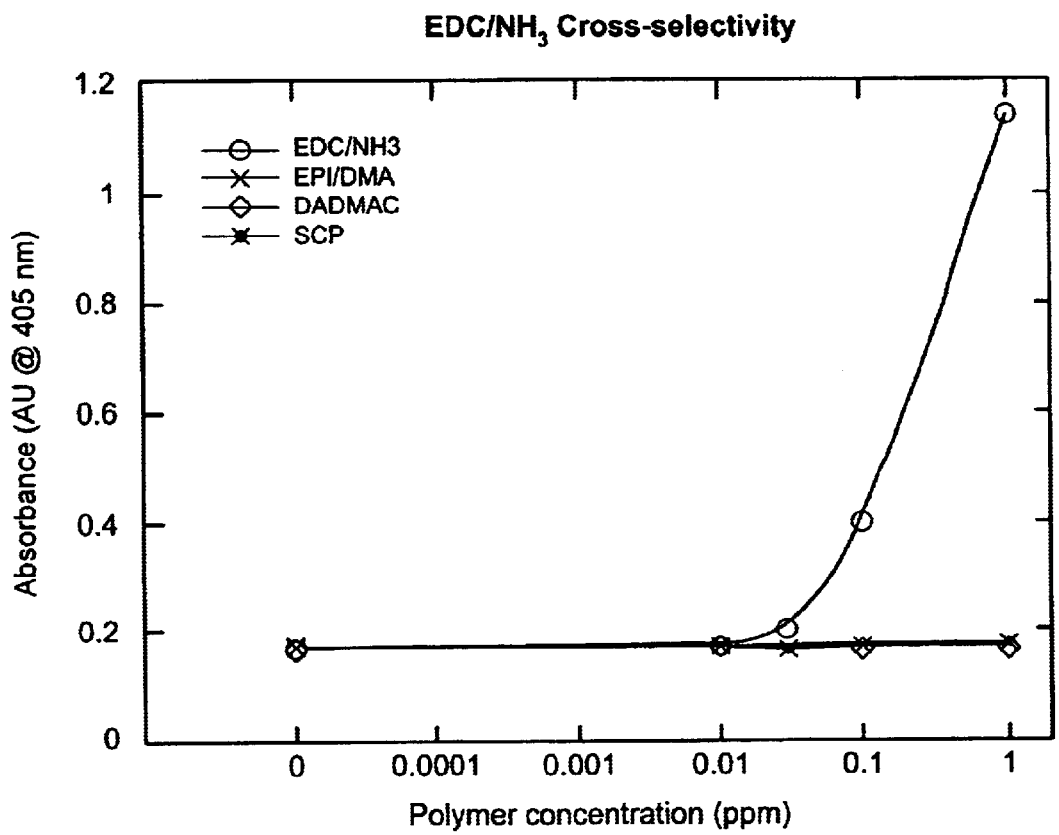
FIG. 15 graphically illustrates the binding profile of the monoclonal antibody from the hybridoma cell line having an affinity for EDC/$NH_3$ polymer.

The adsorption of polymer by raw water was investigated further. Previous experiments showed that ≈90% of added polymer adsorbed when mixed with river water at concentrations up to 3 ppm. In the previous experiments the polymer spiked river water was not stirred for extended periods of time prior to analysis. Distilled water and River B water were spiked to a concentration of 1 ppm of polymer A actives. Aliquots of these spiked samples were placed in 4 oz. glass jars, allowing half of them to sit unstirred at room temperature, while the other half were stirred for 35 minutes. After this time all the samples were analyzed by immunoassay. All the samples were then allowed to sit, covered, overnight at room temperature, and were reanalyzed the next day. The resulting absorbencies, ranked in decreasing order, are compared in FIG. 12. The previously mentioned studies of polymer capacity, which yielded ≈90% adsorption, were prepared exactly as the 'River B unstirred' sample in this experiment. It is apparent from the graph that both the stirring and aging processes decreased the amount of free polymer from what was observed after simple mixing.

EXAMPLE 14

The selectivity of Polymer D immunoassay for an epichlorohydrin/dimethyl amine (Epi/DMA) containing product was investigated. Standards containing 10 to 300 ppb actives of Polymer E were analyzed in triplicate by the Polymer D immunoassay. Though the response was lower on an actives basis than previously observed Polymer D responses, the assay did detect between 50 and 100 ppb actives of Polymer E.

EXAMPLE 15

The reduction of coagulant aquatic toxicity in waters containing humic acid or other anionic material was investigated. It has been observed that the toxicity of Polymer D does not significantly increase with exposure time (see Table 1).

TABLE 1

Toxic concentration of Polymer D vs. exposure time.

| Exposure Time (min.) | (ppm of Polymer D) |
|---|---|
| 5 | 3.4219 to 4.0710 |
| 10 | 2.8762 to 3.7060 |
| 30 | 2.4593 to 3.1410 |

For the initial humic acid studies 22 ppm of Polymer D was combined with 0.5, 5 and 10 ppm of humic acid, and 66 ppm of Polymer D with 0.5 ppm humic acid in a subsequent study. The toxicity of the solutions was observed by after 5 minutes. TOC concentrations in the solutions were also measured (See Table 2).

TABLE 2

Summary of toxicity and TOC levels for mixtures of Polymer D and humic acid.

| Polymer D concentration (ppm) | Humic acid concentration (ppm) | (ppm Polymer D) | TOC (ppm) |
|---|---|---|---|
| 22.22 | 0.5 | nt | 6.8 |
| 22.22 | 5 | nt | 11.09 |
| 22.22 | 10 | nt | 0 |
| 66.6 | 0.5 | 4.3913 | nm | nt: non-toxic at the concentrations tested, nm: not measured.

Changes can be made in the composition, operation and arrangement of the various cell lines, monoclonal antibodies, steps and procedures described herein without departing from the concept and scope of the invention as defines in the following claims.

What is claimed is:

1. A monoclonal antibody which binds to a water treatment polymer wherein the water treatment polymer is selected from the group consisting of epichlorohydrin/dimethylamine polymers, poly(diallyldimethylammonium chloride)polymers, ethylenedichloride/ammonium polymers, melamine formaldehyde co-polymers, dithiocarbamate and polymeric dithiocarbamate.

2. A method of manufacturing a monoclonal antibody having an affinity to a water treatment polymer, wherein the water treatment polymer is selected from the group consisting of epichlorohydrin/dimethylamine polymers, poly (diallyldimethylammonium chloride)polymers, ethylenedichloride/ammonium polymers, melamine formaldehyde co-polymers, dithiocarbamate and polymeric dithiocarbamate, the method including the steps of:
   a) immunizing a mammal with the water treatment polymer bound to a carrier protein;
   b) preparing a hybridoma cell producing the monoclonal antibody from a cell from the immunized mammal;
   c) cloning said hybridoma cell to produce a cell line; and
   d) extracting said monoclonal antibody from said hybridoma cell line.

3. The method of claim 2, wherein the carrier protein is keyhole limpet hemacyanin or bovine serum albumin.

4. The method of claim 2, wherein the mammal is a mouse.

5. A method for determining a concentration of a water treatment polymer in a fluid, wherein the water treatment polymer is selected from the group consisting of epichlorohydrin/dimethylamine polymers, poly (diallyldimethylammonium chloride)polymers, ethylenedichloride/ammonium polymers, melamine formaldehyde co-polymers, dithiocarbamate and polymeric dithiocarbamate, the method comprising:
   a) incubating a sample of the fluid containing the water treatment polymer with a capture antibody which binds to the water treatment polymer, the antibody being bound to a solid carrier, and a labeled second antibody which binds to the water treatment polymer to create an antibody-polymer-antibody complex, wherein the capture antibody or labeled second antibody is a monoclonal antibody;
   b) washing the antibody-polymer-antibody complex to separate labeled, bound antibody from labeled, unbound antibody; and
   c) measuring the amount of bound or unbound labeled antibody to determine the concentration of the water treatment polymer in the fluid.

6. The method of claim 5, wherein washing the complex is accomplished by filtration, magnetic separation, decanting, centrifugation or chromatography.

7. The method of claim 5, wherein the labelled antibody is labelled with a compound, wherein the compound is an enzyme, colored particle, fluorescent molecule, luminescent molecule, metal or radioisotope.

8. A method for determining a concentration of a water treatment polymer in a fluid, wherein the water treatment polymer is selected from the group consisting of epichlorohydrin/dimethylamine polymers, poly (diallyldimethylammonium chloride)polymers, ethylenedichloride/ammonium polymers, melamine formaldehyde co-polymers, dithiocarbamate and polymeric dithiocarbamate, the method comprising:

a) incubating a sample of the fluid containing the water treatment polymer with known quantities of labeled water treatment polymer and a capture antibody which binds to the water treatment polymer, the antibody being bound to a solid carrier to create an antibody-polymer mixture, wherein the capture antibody is a monoclonal antibody;

b) washing the antibody-polymer mixture to separate unbound from bound labeled water treatment polymer; and c) measuring the amount of bound or unbound labeled water treatment polymer to determine the concentration of water treatment polymer in the fluid.

9. The method of claim 8, wherein washing the antibody-polymer mixture is accomplished by filtration, magnetic separation, decanting, centrifugation or chromatography.

10. A method for determining a concentration of a water treatment polymer in a fluid, wherein the water treatment polymer is selected from the group consisting of epichlorohydrin/dimethylamine polymers, poly(diallyldimethylammonium chloride)polymers, ethylenedichloride/ammonium polymers, melamine formaldehyde co-polymers, dithiocarbamate and polymeric dithiocarbamate, the method comprising incubating a sample of the fluid containing the water treatment polymer with a monoclonal antibody which binds to the water treatment polymer to form an antibody-polymer complex and measuring the amount of antibody-polymer complex formed.

11. A method for determining a concentration of a water treatment polymer in a fluid, wherein the water treatment polymer is selected from the group consisting of epichlorohydrin/dimethylamine polymers, poly(diallyldimethylammonium chloride) polymers, ethylenedichloride/ammonium polymers, melamine formaldehyde co-polymers, dithiocarbamate and polymeric dithiocarbamate, the method comprising:

a) incubating a sample of the fluid containing the water treatment polymer with a water treatment polymer bound to a solid carrier and known quantities of labeled monoclonal antibody which bind to the water treatment polymer to create an antibody-polymer mixture;

b) washing the antibody-polymer mixture to separate unbound from bound labeled antibody; and c) measuring the amount of bound or unbound labeled antibody to determine the concentration of water treatment polymer in the fluid.

* * * * *